(12) United States Patent
Briscoe et al.

(10) Patent No.: US 8,776,622 B2
(45) Date of Patent: Jul. 15, 2014

(54) APPARATUS FOR MOBILE COLLECTION OF ATMOSPHERIC SAMPLE FOR CHEMICAL ANALYSIS

(75) Inventors: Matthew Briscoe, Zionsville, IN (US); Brent Rardin, Lafayette, IN (US); Dennis Barket, Jr., Lafayette, IN (US)

(73) Assignee: FLIR Detection, Inc., Stillwater, OK (US)

( * ) Notice: Subject to any disclaimer, the term of this patent is extended or adjusted under 35 U.S.C. 154(b) by 0 days.

(21) Appl. No.: 13/436,421

(22) Filed: Mar. 30, 2012

(65) Prior Publication Data

US 2012/0197544 A1    Aug. 2, 2012

Related U.S. Application Data

(62) Division of application No. 12/216,027, filed on Jun. 27, 2008, now Pat. No. 8,146,448.

(60) Provisional application No. 60/929,506, filed on Jun. 29, 2007.

(51) Int. Cl.
  *G01N 1/24* (2006.01)
  *G01N 1/40* (2006.01)
  *G01N 33/00* (2006.01)
  *G01N 1/22* (2006.01)

(52) U.S. Cl.
  CPC .......... *G01N 1/2273* (2013.01); *G01N 33/0004* (2013.01)
  USPC ..................... 73/863.31; 73/31.02; 73/863.21; 73/863.23; 73/863.25; 73/863.71

(58) Field of Classification Search
  CPC ... G01N 1/2273; G01N 1/24; G01N 33/0004; G01N 2001/2202; G01N 2001/2214; G01N 2033/0004
  USPC ......... 73/31.02, 198, 863.01–863.03, 863.21, 73/863.23, 863.25–863.31, 863.71, 73/864.34, 864.63
  See application file for complete search history.

(56) References Cited

U.S. PATENT DOCUMENTS

| | | | |
|---|---|---|---|
| 3,241,371 A | 3/1966 | Horeth | |
| 4,091,674 A | 5/1978 | Amey | |

(Continued)

FOREIGN PATENT DOCUMENTS

| | | |
|---|---|---|
| GB | 2056304 | 3/1981 |
| GB | 0811814.3 | 10/2008 |

(Continued)

OTHER PUBLICATIONS

CDS Analytical, Inc., Dynatherm Chemical Agent Monitors Home Page (Mar. 11, 2008). Http://www.cdsanalytical.com/dynatherm.html, pp. 1-2.

(Continued)

*Primary Examiner* — Thomas P Noland
(74) *Attorney, Agent, or Firm* — Wells St. John P.S.

(57) ABSTRACT

Portable devices and related methods for collecting and storing atmospheric samples for subsequent chemical analysis are provided. A sample cartridge according to one implementation includes self-sealing inlet and outlet ports configured to close automatically when not in use, and a sample retention portion between the inlet and outlet ports that is adapted to trap an atmospheric sample. The sample cartridge may also include a memory device for recording data regarding the sample. Another embodiment provides a portable sampler configured to removably secure a self-sealing sample cartridge. A portable sampling device may also be used with an analytical instrument. The analytical instrument may analyze the sample and read the data recorded on the sample cartridge's memory.

12 Claims, 21 Drawing Sheets

(56) References Cited

U.S. PATENT DOCUMENTS

| | | | |
|---|---|---|---|
| 4,170,901 | A | 10/1979 | Conkle et al. |
| 4,546,659 | A | 10/1985 | Gill et al. |
| 4,584,887 | A | 4/1986 | Galen |
| 4,718,268 | A | 1/1988 | Reid et al. |
| 4,760,881 | A | 8/1988 | Long et al. |
| 5,124,274 | A | 6/1992 | Ohki et al. |
| 5,138,889 | A | 8/1992 | Conrad |
| 5,142,143 | A | 8/1992 | Fite et al. |
| 5,288,310 | A | 2/1994 | Peters et al. |
| 5,402,668 | A | 4/1995 | Murakami et al. |
| 5,437,199 | A | 8/1995 | Kaplan |
| 5,500,369 | A | 3/1996 | Kiplinger |
| 5,551,278 | A | 9/1996 | Rounbehler et al. |
| 5,585,575 | A | 12/1996 | Corrigan et al. |
| 5,597,535 | A | 1/1997 | Schaedlich et al. |
| 5,826,577 | A | 10/1998 | Perroz, Jr. et al. |
| 6,167,767 | B1 | 1/2001 | Mengel et al. |
| 6,230,573 | B1 | 5/2001 | Schulten et al. |
| 6,321,609 | B1 | 11/2001 | Mengel et al. |
| 6,339,965 | B1 | 1/2002 | Pasquereau et al. |
| 6,446,514 | B1 | 9/2002 | Danylewych-May et al. |
| 6,450,784 | B2 | 9/2002 | Newcomer |
| 6,477,905 | B1 | 11/2002 | Mitra |
| 6,477,906 | B1 | 11/2002 | Peterson |
| 6,723,056 | B1 | 4/2004 | Alving et al. |
| 6,819,253 | B2 | 11/2004 | Albro et al. |
| 6,989,130 | B2 | 1/2006 | Deshmukh |
| 7,161,142 | B1 | 1/2007 | Patterson et al. |
| 7,171,312 | B2 | 1/2007 | Steinthal et al. |
| 7,227,472 | B1 | 6/2007 | Roe |
| 7,600,439 | B1 | 10/2009 | Patterson et al. |
| 7,874,221 | B1 | 1/2011 | Mayeaux |
| 7,875,109 | B1 | 1/2011 | Mayeaux |
| 7,921,739 | B2 | 4/2011 | Fjerdingstad et al. |
| 2004/0123679 | A1 | 7/2004 | Coleman et al. |
| 2004/0224422 | A1 | 11/2004 | Bonne et al. |
| 2008/0229805 | A1 | 9/2008 | Barket et al. |
| 2013/0174646 | A1* | 7/2013 | Martin, David .............. 73/31.02 |

FOREIGN PATENT DOCUMENTS

| | | | |
|---|---|---|---|
| RU | 2006021 C1 | 1/1994 | |
| WO | WO 0026405 A1 * | 5/2000 | ............... C12Q 1/68 |
| WO | WO 2005/047865 | 5/2005 | |
| WO | WO 2005/103641 | 11/2005 | |
| WO | WO 2006/062906 | 6/2006 | |

OTHER PUBLICATIONS

Hi-Q Environmental Products Co., HVP-3800AFC & HVP-3500AFC Series Samplers Information Page (Mar. 11, 2008). http://store.hi-q.net/Item/HVP4200AFCHVP4300AFCSeries.html, pp. 1-2.

Hi-Q Environmental Products Co., HVP-4200AFC & HVP-4300AFC Series Information Page (Mar. 11, 2008). http://store.hi-q.net/item/HVP4200AFCHVP4300AFCSeries.html, pp. 1-2.

Inficon, Hapsite Accessory Catalog 2007 (Mar. 11, 2008). Http://www.infocon.com/download/en/dild30a%20HAPSITE%20Accesory%20Catalog.pdf, Cover page, 2nd page, pp. TOC-1 to TOC-4, 1-1 to 1-16, 2-1 to 2-20 and 3-1 to 3-24.

Inficon, Hapsite Chemical Indentification System Brochure 2003 (Mar. 12, 2008). Http://www.inficon.com/download/en/HAPSchemiidentsys.pdf, 2 pages.

Inficon, Hapsite Headspace Sampling System Brochure (Mar. 11, 2008). http://www.inficonchemicalidentificationsystems.com/en/pdf/HAPSITEheadspace.pdf, copyright 2003, 2 pages.

Inficon, Hapsite Situprobe Brochure 2007 (Mar. 11, 2008). Http://www.inficon.com/download/en/situprobe.pdf, 2 pages.

Inficon, Hapsite Smart Chemical Identification System Brochure 2007 (Mar. 11, 2008). Http://www.inficon.com/download/en/haps-smart.pdf, 2 pages.

Inficon, Hapsite Smart Plus Chemical Identification System Brochure 2007 (Mar. 11, 2008). Http://www.inficon.com/download/en/HAPSITE_Smart_Plus_LR.pdf, 2 pages.

Inficon, Hapsite Viper Chemical Identification System with 267 Surface Sampler Brochure 2006 (Mar. 11, 2008). Http://www.inficon.com/download/en/hapsitev.pdf, 2 pages.

Inficon, Inficon Product Index (Mar. 12, 2008). Http://www.inficon.com/en/productindex.html, copyright 2007, pp. 1-4.

Inficon, Scentograph CMS100 Brochure 2003 (Mar. 11, 2008). http://www.inficonchemicalmonitoringsystems.com/en/Scentographcms100.html, 2 pages.

Inficon, Scentograph CMS200 Brochure 2003 (Mar. 11, 2008). http://www.inficonchemicalmonitoringsystems.com/en/pdf/Scentograph_CMS200_Brochure.pdf, 2 pages.

Markes International Ldt., "Chemical Warfare Agents & Homeland Security" (Mar. 11, 2008). http://www.marks.com/en/chemicalWarfare/default.aspx, pp. 1-2.

Spectrex Corp., Operating Manual PAS-500 Personal Air Sampler (Mar. 11, 2008). http://www.spectrex.com/html_files/pdf/PAS500manual.pdf, 2 pages.

Spectrex Corp., Perating Manual PAS-2000 Personal Air Sampler (Mar. 11, 2008). http://www.spectrex.com/html_files/pdf/PAS-2000%20manual.pdf, cover page and pp. 1-8, Jan. 2006.

Teledyne Technologies, Inc., Teledyne Tekmar Products (Mar. 11, 2008). Http://teledynetekmar.com/products/index.asp, copyright 2006, 1 page.

V. Camel et al., "Trace Enrichment Methods for the Determination of Organic Pollutants in Ambient Air", Journal of Chromatography A, vol. 710, No. 1, pp. 3-19 (1995).

* cited by examiner

APPARATUS FOR MOBILE COLLECTION OF ATMOSPHERIC SAMPLE FOR CHEMICAL ANALYSIS

CROSS-REFERENCE TO RELATED APPLICATION

This application is a divisional of U.S. patent application Ser. No. 12/216,027 which was filed Jun. 27, 2008, entitled "Apparatus for Mobile Collection of Atmospheric Sample for Chemical Analysis," which claims the benefit of U.S. Provisional Application No. 60/929,506, filed Jun. 29, 2007, entitled "Apparatus for Mobile Collection of Atmospheric Sample for Chemical Analysis", the entirety of each of which is incorporated herein by reference.

FIELD

The present disclosure relates to hand-held or portable devices and related methods for collecting and storing atmospheric samples for subsequent chemical analysis.

BACKGROUND

Recently, there has been an increased demand for portable devices to collect atmospheric samples for chemical analysis. Currently, several types of portable samplers exist, such as that disclosed in PCT Publication No. WO/2006/062906, which is hereby incorporated by reference. Other examples of portable samplers may be found at U.S. Pat. No. 7,171,312 and U.S. Pat. No. 6,321,609.

Often these samplers suffer from a variety of drawbacks. For example, in many applications, the sampler must be decontaminated after sample collection but before analysis of the sample. In current applications, however, it is often difficult to decontaminate the sampler without affecting the sample since introduction of common decontamination cleaning agents into the sampler can destroy the collected sample. In addition, often the location where the sample is stored in the sampler is subject to contamination from other sources if not properly sealed. Further, the samplers often have no ability to store information regarding the sample or environmental conditions in the sampling environment. Thus, the operator must separately record this information. In some instances, this information is either not properly recorded or is not properly correlated to the correct sample.

It is accordingly an object of the disclosure to address these issues with handheld samplers.

SUMMARY

Apparatus consistent with one embodiment provide a sample cartridge for storing an atmospheric sample. The sample cartridge comprises a self-sealing inlet port configured to automatically close when the inlet port is not in use; a self-sealing outlet port configured to automatically close when the outlet port is not in use; and a sample retention portion in fluid communication with and disposed between the inlet port and outlet port and adapted to trap an atmospheric sample.

Apparatus consistent with another embodiment provide a portable sampler for collecting a sample. The portable sampler includes a portable housing having an interior portion. The portable housing is configured to removably secure a sample cartridge within the interior portion, the sample cartridge having a self-sealing inlet port and a self-sealing outlet port. The portable housing is further configured to open the self-sealing inlet port and the self-sealing outlet port when the sample is secured therein. A portable sampler also includes a sample inlet in communication with an area outside the housing and configured to establish fluid communication with the sample cartridge when the sample cartridge is secured; a pump configured to draw a sample into the sample cartridge through the sample inlet when the sample cartridge is secured; a processor-configured to operate the sampler; and an input/output interface.

A system consistent with another embodiment provides a sampler, an analytical instrument, and a sample cartridge configured to be removably inserted within the sampler. The sample cartridge includes a first port including a first valve configured to self-close when the sample cartridge is not inserted within the sampler; a second port including a second valve configured to self-close when the sample cartridge is not inserted within the sampler; and a sample trap in fluid communication with the first port and the second port.

An additional embodiment provides a method of collecting and analyzing a sample. The method includes providing a sample cartridge, the sample cartridge comprising a self-sealing inlet port configured to automatically close when the inlet port is not in use; a self-sealing outlet port configured to automatically close when the outlet port is not in use; and a sample trap in fluid communication with and disposed between the inlet port and outlet port and adapted to trap a sample. The method also includes providing a sampler having a sampler inlet and an interior portion, the interior portion being configured to releasably receive the sample cartridge; inserting the sample cartridge into the sampler, whereby at least one of the self-sealing inlet port and self-sealing outlet port is opened; and, collecting a sample through the sampler inlet and into the sample trap.

Additional objects and advantages will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments and together with the description, serve to explain the principles of the disclosure. Additionally, it is contemplated that individual features of one embodiment may be added to, or substituted for, individual features of another embodiment. Accordingly, it is within the scope of this disclosure to cover embodiments resulting from substitution and replacement of different features between different embodiments.

DESCRIPTION OF THE EMBODIMENTS

Reference will now be made in detail to the present exemplary embodiments, examples of which are illustrated in the accompanying drawings.

One embodiment entails a hand-held or otherwise portable sampler 300 for collecting and storing atmospheric samples for subsequent analysis, such as, e.g., chemical analysis. The atmospheric samples collected by the sampler 300 may include a matrix, such as, e.g., atmospheric gasses like oxygen and nitrogen, that contain materials to be analyzed, including potentially harmful chemical contaminants or pollutants, biological materials such as, e.g., anthrax spores, and radioisotopes to be subsequently analyzed. Hereinafter, the materials collected by the sampler 300 will be referred to as analytes.

Figure 1A:
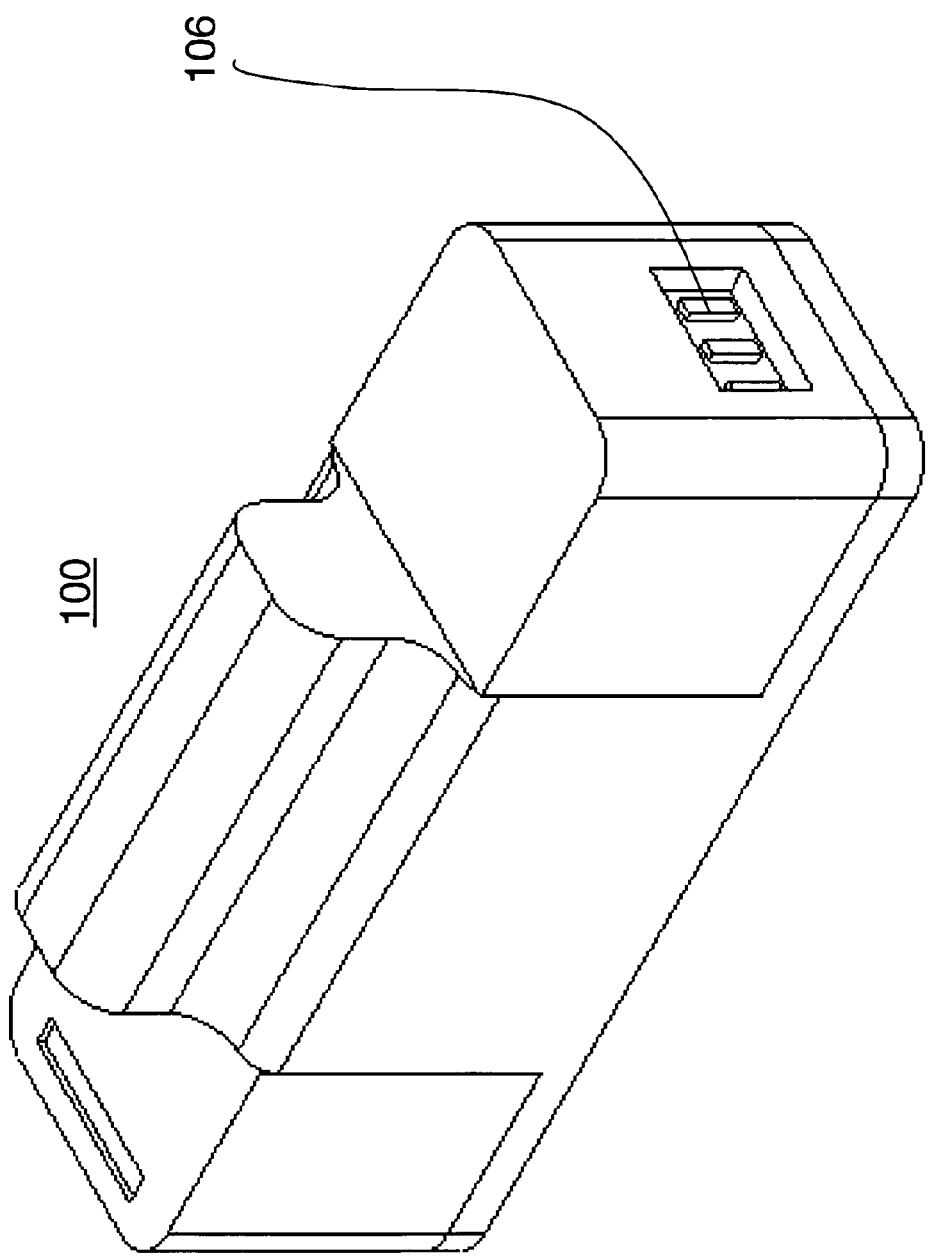
FIG. 1A is a perspective view of a cartridge for a handheld sampler in accordance with one embodiment.
Figure 1B:
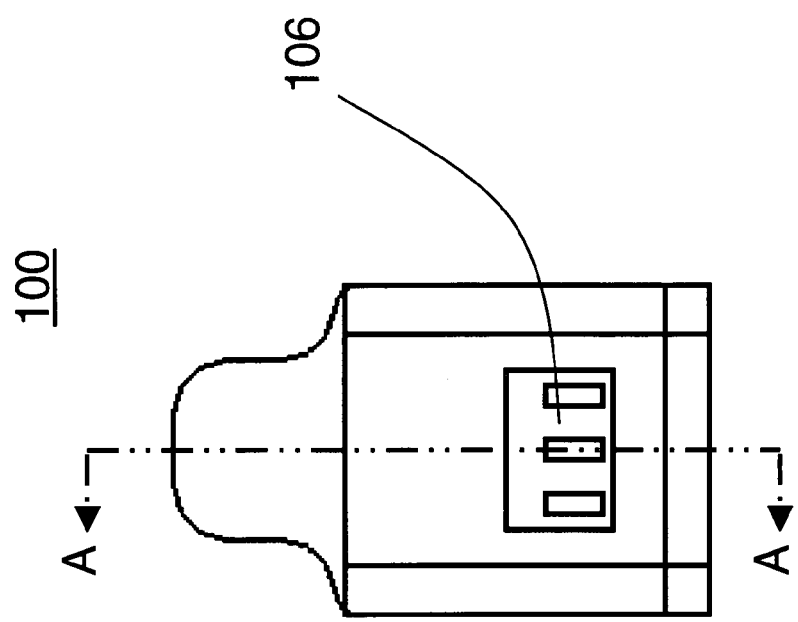
FIG. 1B is a front view of a cartridge for a handheld sampler in accordance with one embodiment.
Figure 1C:
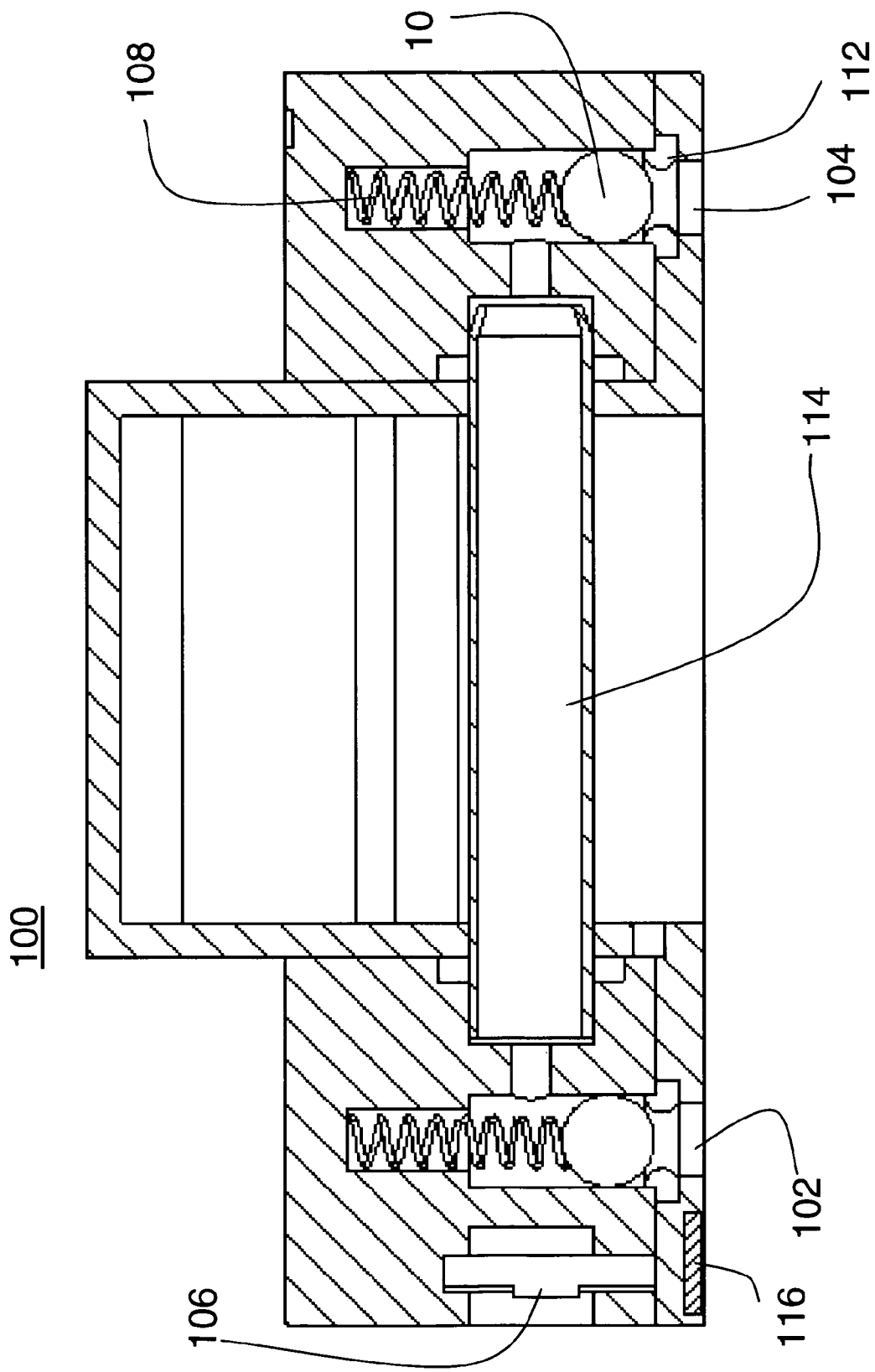
FIG. 1C is a side cross-section view of a cartridge for a handheld sampler along line A-A of FIG. 1B in accordance with one embodiment.
Figure 2A:
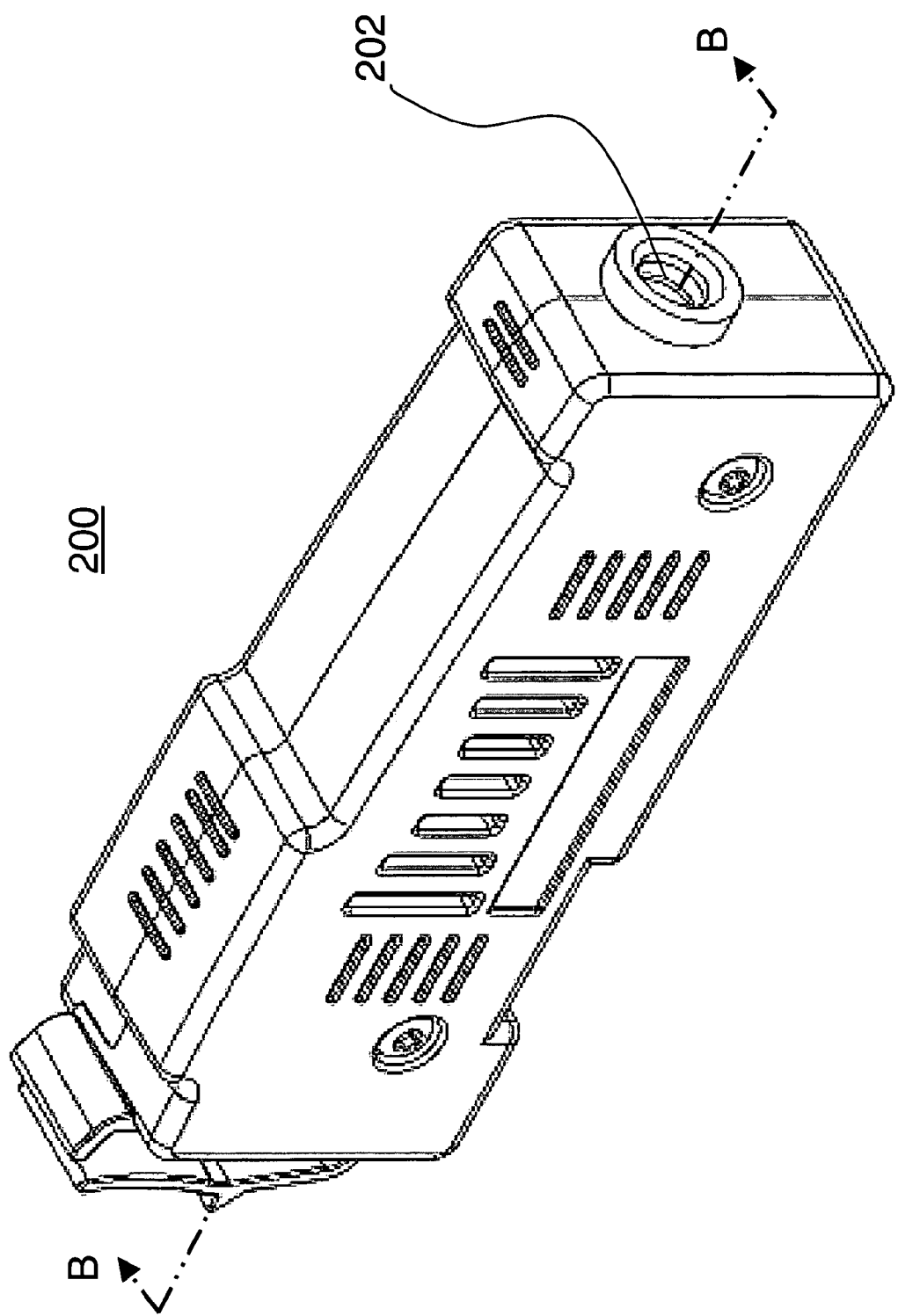
FIG. 2A is a perspective view of a cartridge for a handheld sampler in accordance with an additional embodiment.
Figure 2B:
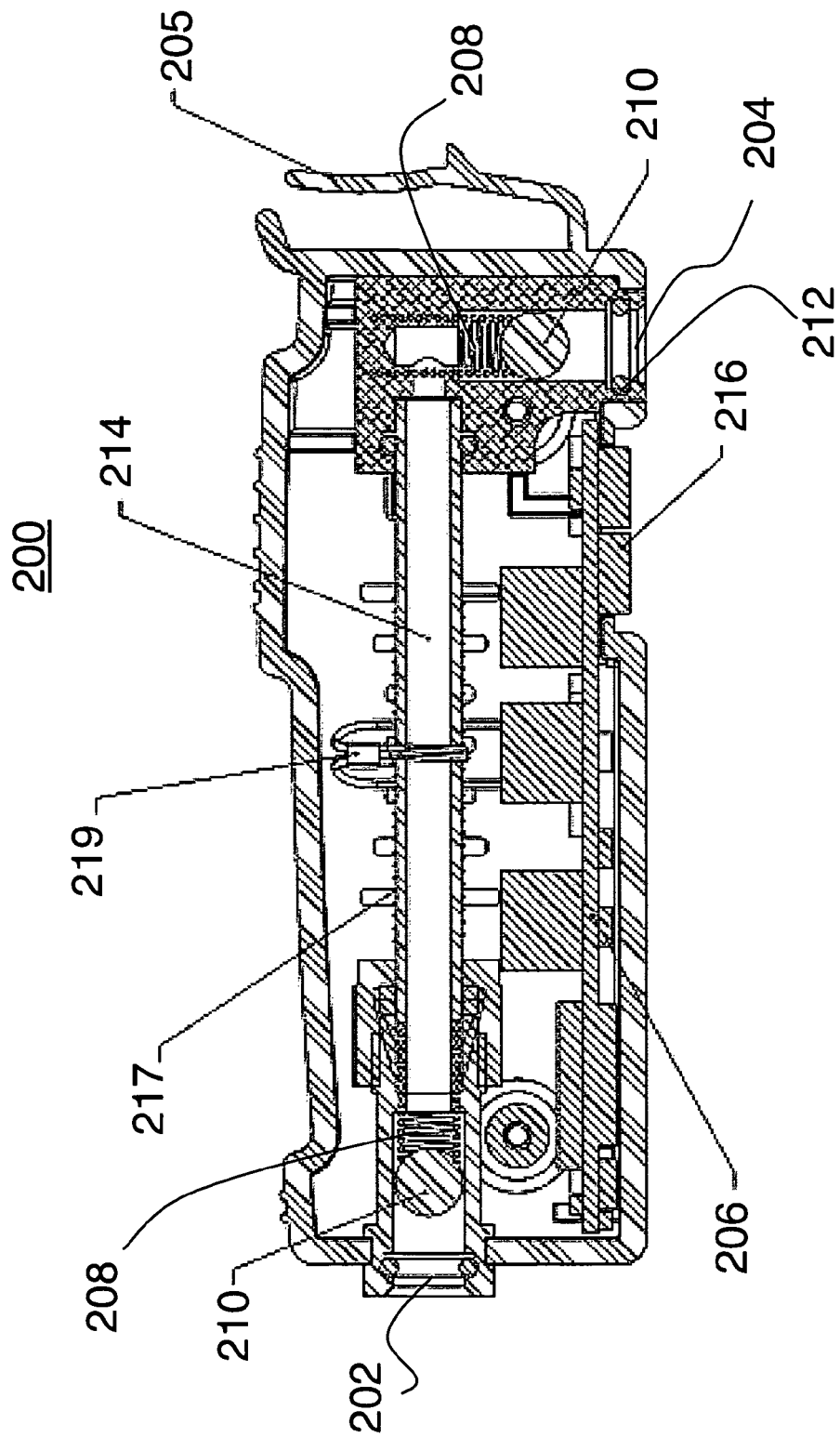
FIG. 2B is a side cross-section view of a cartridge for a handheld sampler along line B-B of FIG. 1D in accordance with an additional embodiment.
Figure 4A:
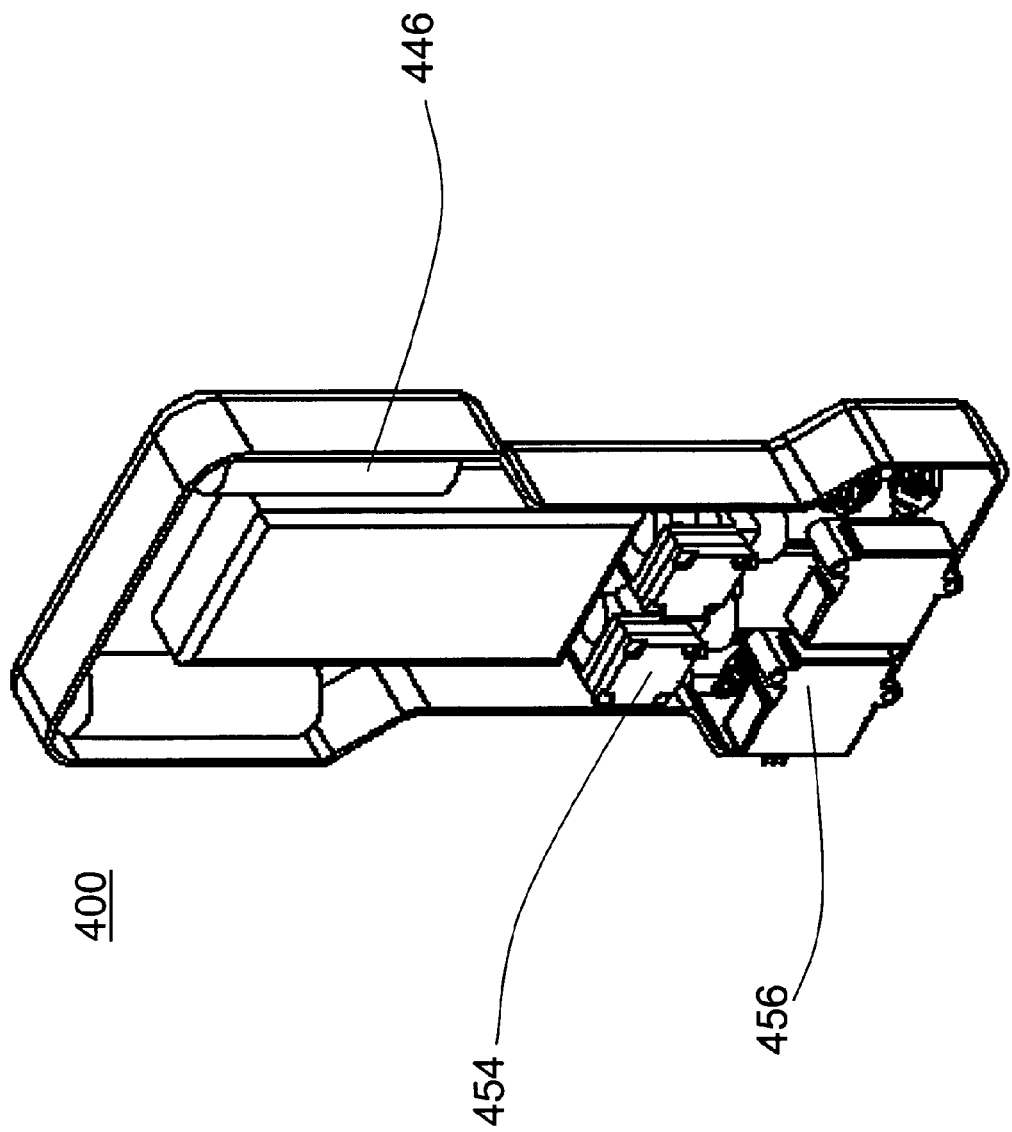
FIG. 4A is a perspective view of a handheld sampler with a cartridge installed in accordance with another embodiment.
Figure 4B:
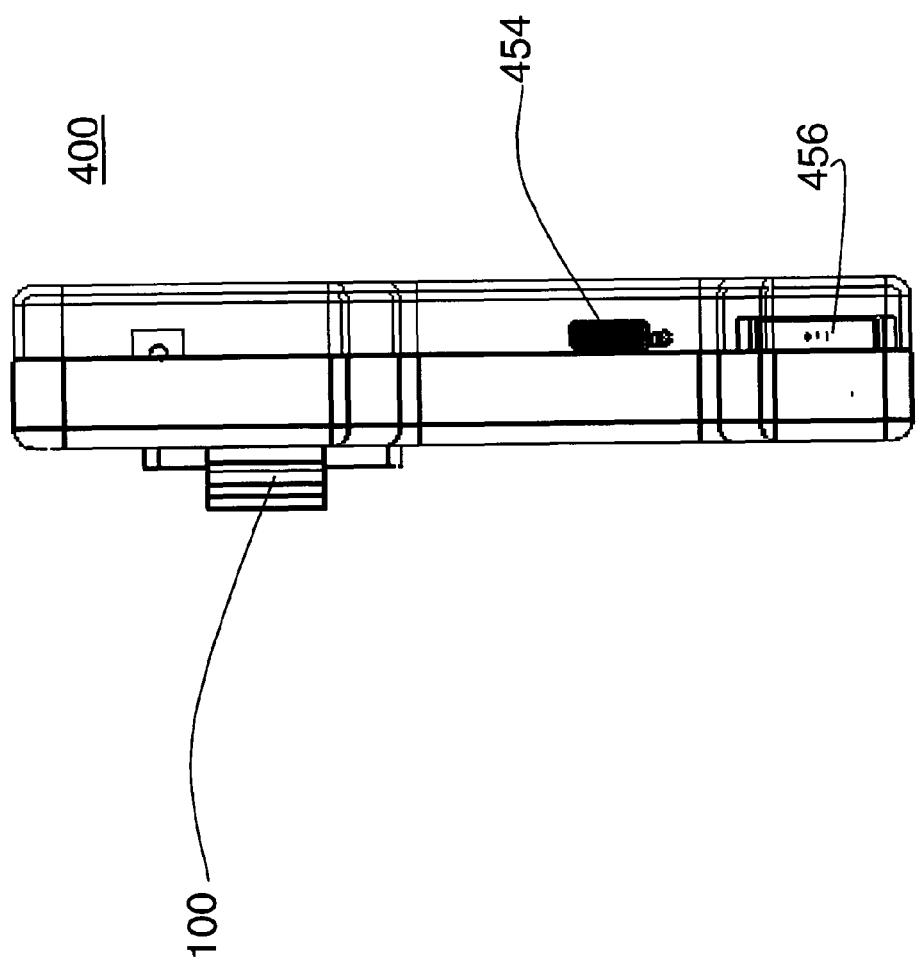
FIG. 4B is a side view of a handheld sampler with a cartridge installed in accordance with another embodiment.
Figure 4C:
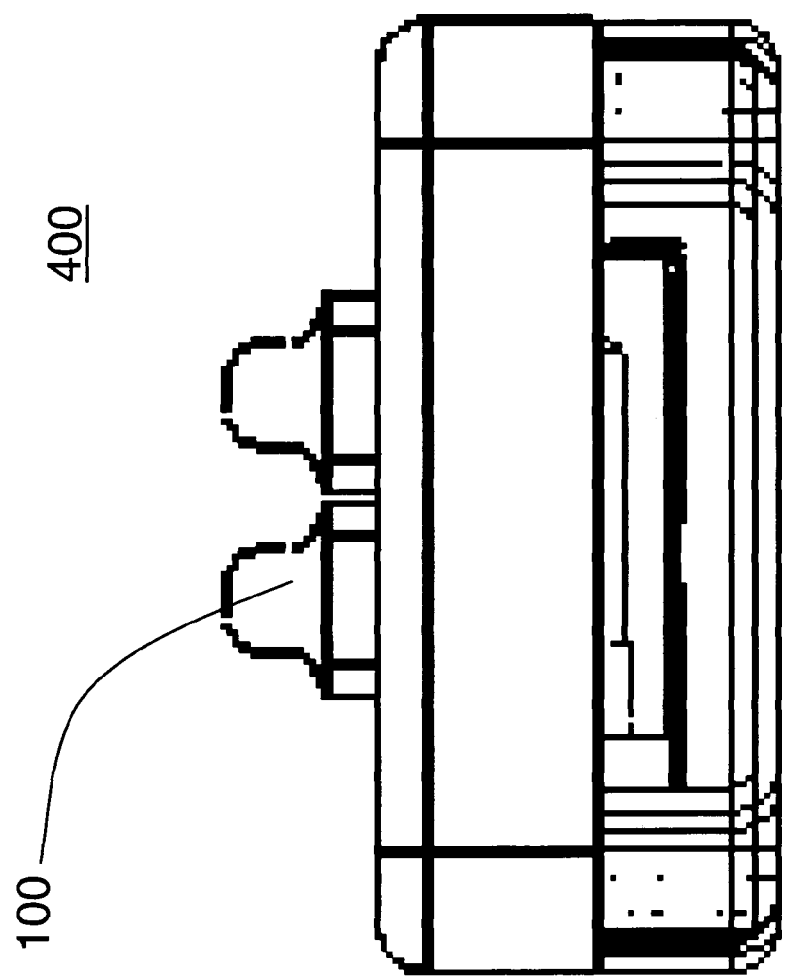
FIG. 4C is a top view of a handheld sampler with a cartridge installed in accordance with another embodiment.
Figure 4D:
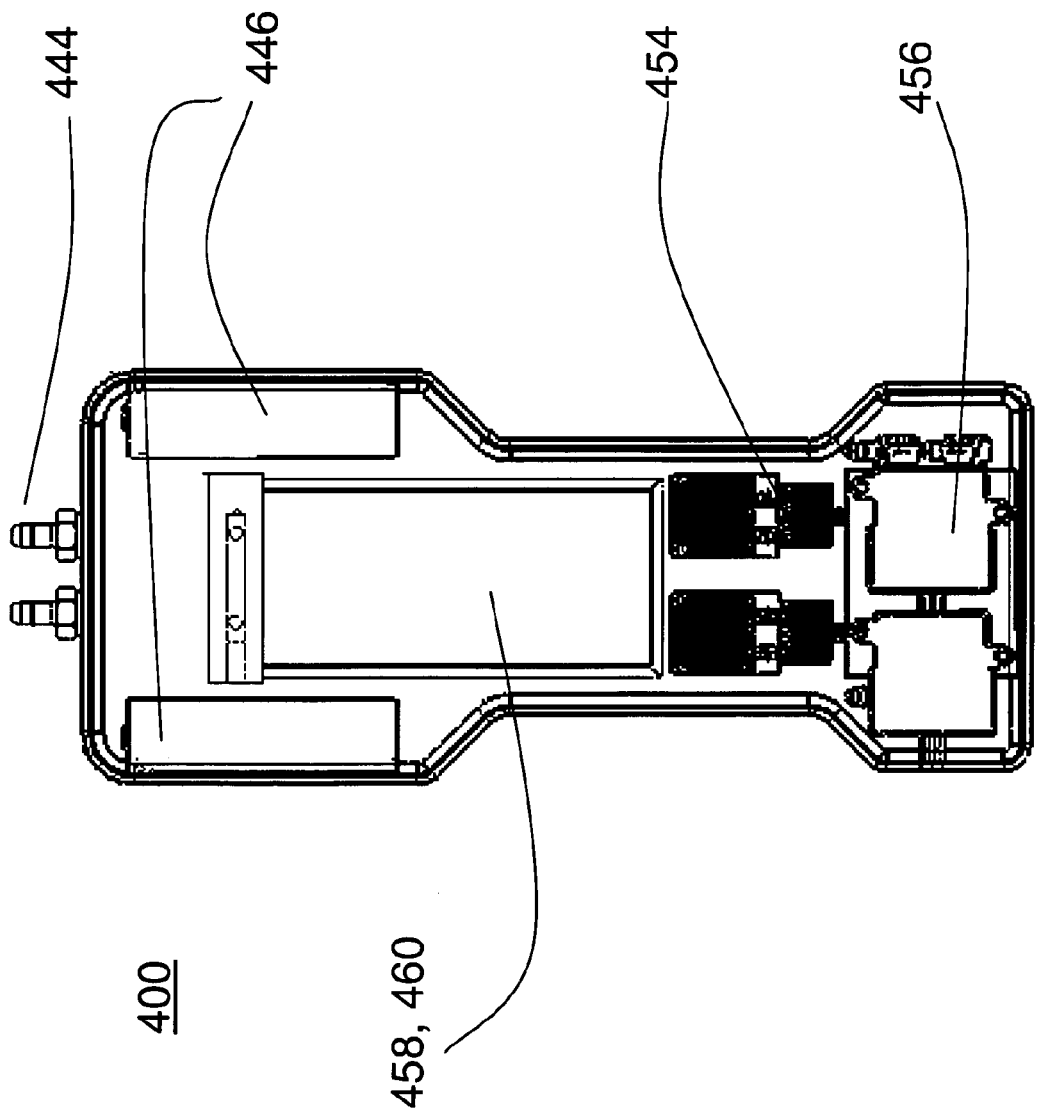
FIG. 4D is a front view of a handheld sampler with a cartridge installed in accordance with another embodiment.
Figure 5A:
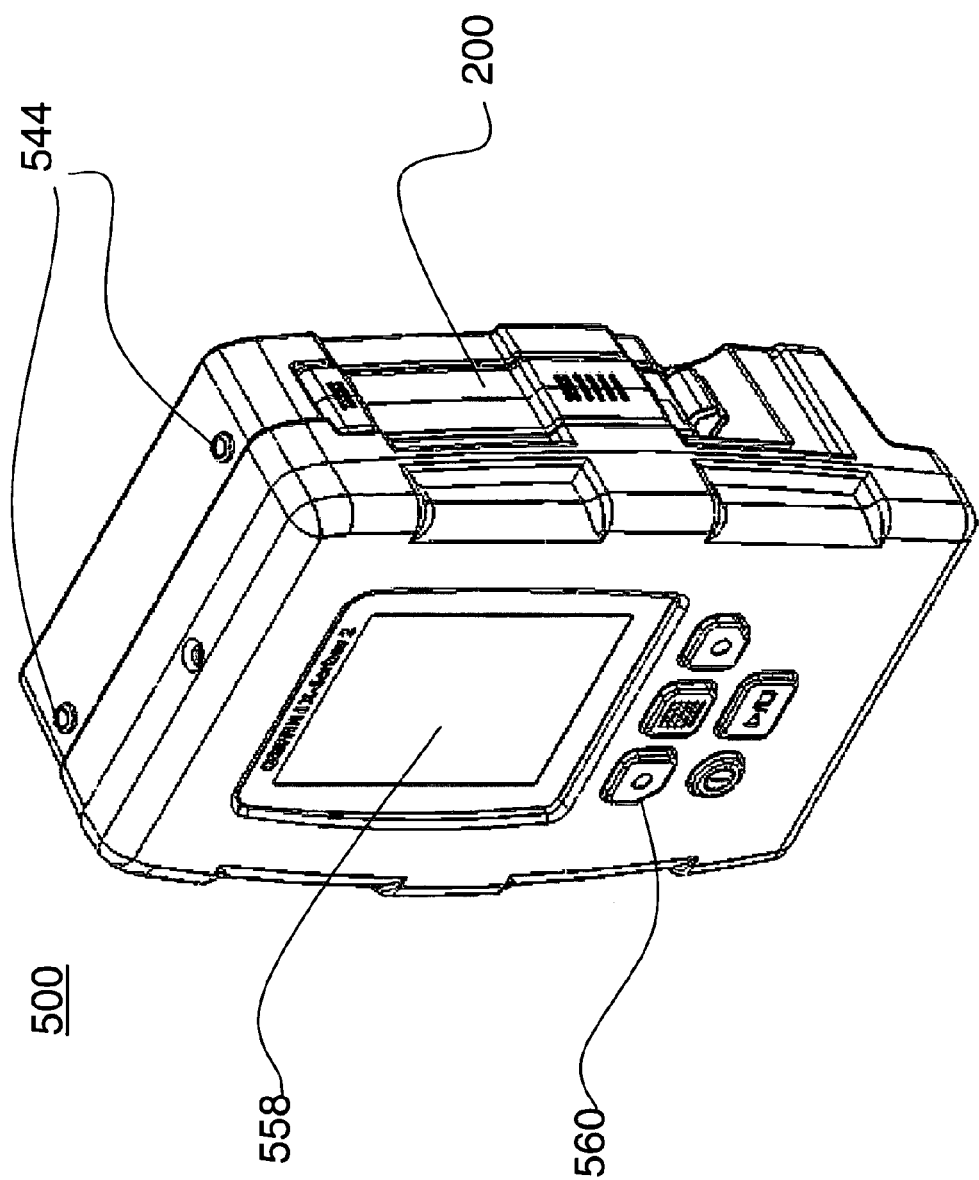
FIG. 5A is a perspective view of a handheld sampler with a cartridge installed in accordance with an additional embodiment.
Figure 5B:
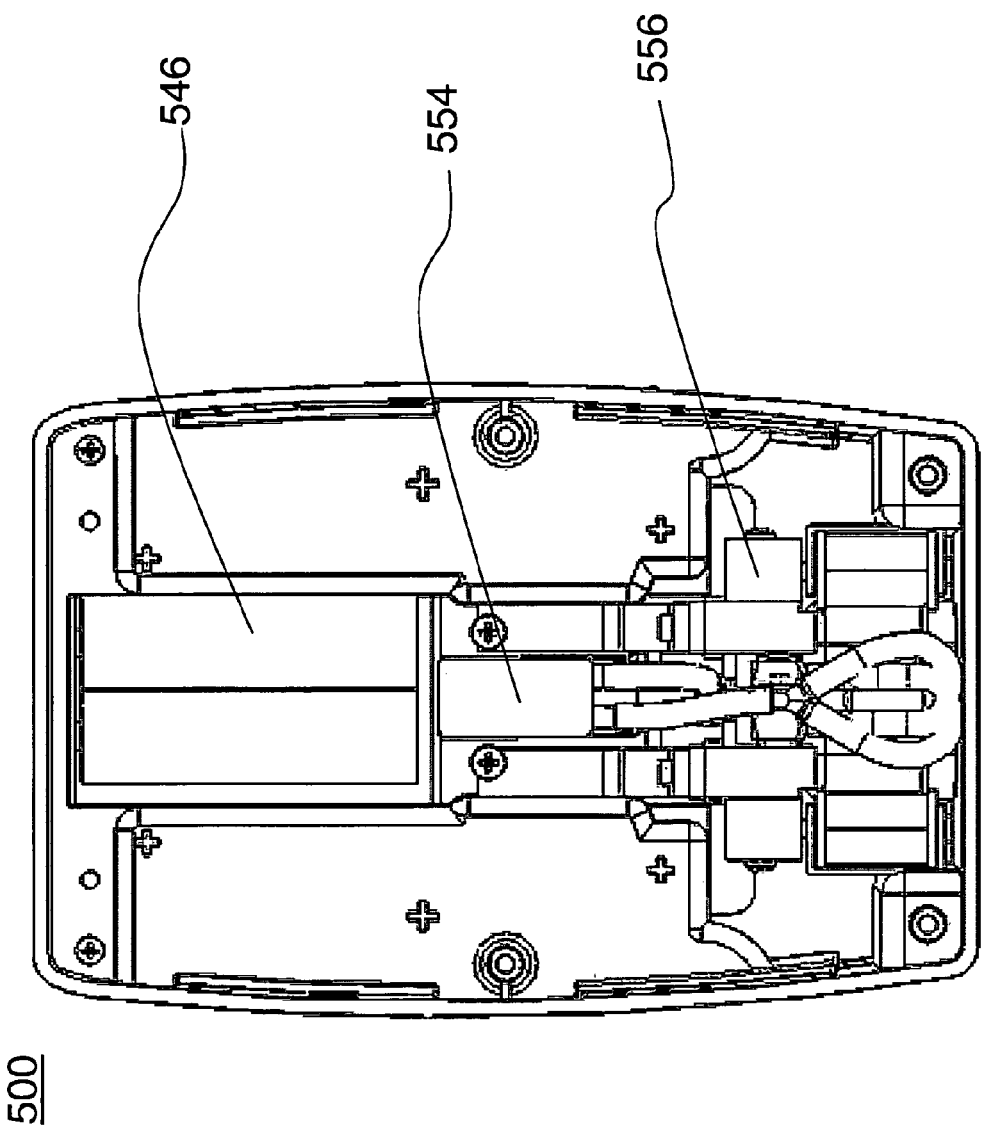
FIG. 5B is a front cross-section of a handheld sampler in accordance with an additional embodiment.
Figure 6:
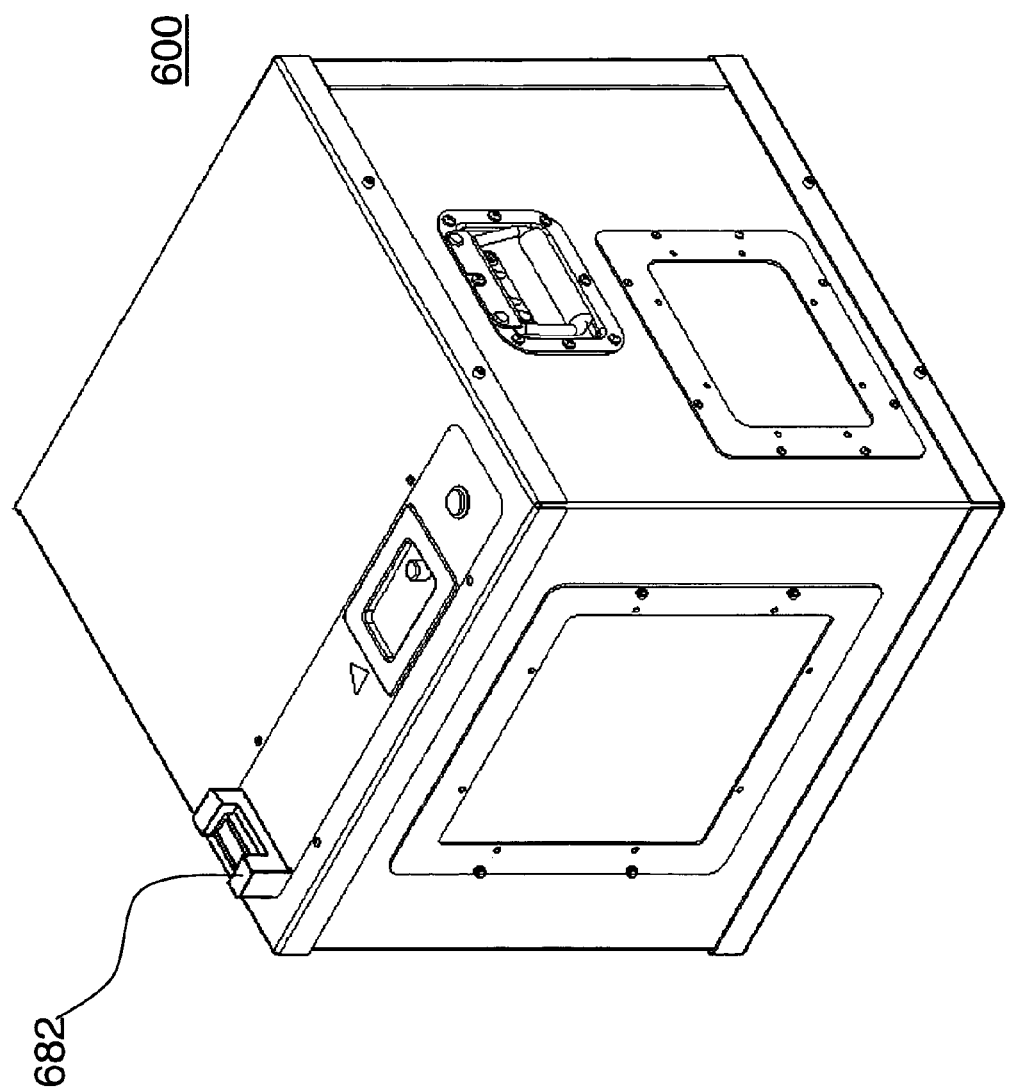
FIG. 6 is a perspective view of an analytical instrument with a cartridge installed in accordance with one embodiment.

In one implementation, the apparatus has three main components: a sample cartridge 100, a sampler 300, and an analytical instrument 600. In operation, a sample cartridge 100 is inserted into the sampler 300 by a user. The user then activates the sampler 300 to trap desired analytes in the cartridge 100. The cartridge 100 is then later removed from the sampler 300 and coupled to an analytical instrument 600 for analysis. One implementation of a sample cartridge 100 is depicted in FIGS. 1A-1C. Another implementation of a sample cartridge 200 is depicted in FIGS. 2A-2B. One implementation of a sampler 300 is depicted in FIGS. 3A-3G. A second implementation of a sampler 400 is depicted in FIGS. 4A-4D. A third implementation of a sampler 500 is depicted in FIGS. 5A-5B. An analytical instrument 600 is depicted in FIG. 6.

A sample cartridge 100 is a device used to trap analytes. When air is pulled/pushed through the cartridge 100 chemical analytes will be stored in the cartridge 100 for later analysis by an analytical instrument 600. In one implementation, the sample cartridge 100 may include sorbent tubes (114 in FIG. 1C) or a Tedlar bag (not shown) to trap analytes. Alternatively, the sample cartridge 100 may comprise disc filters, SPME fibers, evacuated cylinders, and/or any other trap that is known in the art. In addition, different cartridges 100 may be used for different target missions. For example, one cartridge 100 may be used for volatile chemicals, while another cartridge 100 may be for biological agents. This implementation is only exemplary and other methods of trapping analytes in the sample cartridge 100 may be used.

In one implementation, as shown in FIG. 1C, the cartridge 100 has separate inlet 102 and outlet 104 ports, both of which automatically seal the cartridge closed when it is not connected to a sampler 300 or an analytical instrument 600. This design prevents the sample from being contaminated by any other sources and also protects the operator from exposure to the sample. In one implementation, the self-sealing feature can be accomplished using spring force or magnetic force, though any method of self-sealing the inlet 102 or outlet 104 ports may be used.

An embodiment utilizing spring force for self-sealing is illustrated in FIG. 1C. A spring 108 mounted in a cartridge 100 maintains a bearing or valve ball 110 in a normally closed position against seat 112. When a cartridge 100 is inserted, force applied to the bearing or valve ball 110 causes the spring 108 to compress. With the spring 108 compressed, bearing or valve ball 110 separates from seat 112, allowing the transfer of a sample or other material into and/or out of cartridge 100 via inlet 102 and outlet 104 ports.

The use of a self-sealing removable cartridge makes decontamination of the handheld sampler 300 easier. Because the cartridge 100 can be removed from the sampler 300, the external surfaces and the entire flow path of the sampler 300 may be decontaminated without fear of harming the sample. Moreover, the self-sealing nature of the tubes allows the external surfaces of the cartridges 100 to be decontaminated separately before moving the cartridge 100 into a safe zone for analysis.

In another implementation, the cartridge 100 may also include memory for storing data relating to the sample, as shown in FIG. 1A. This data includes any information pertaining to the sample including global positioning system ("GPS") location when sampled, volume of sample collected, date/time stamp, voice data, image data, or any other information to be stored by the user. By storing such information, the devices removes the need for an operator to separately record the information. The illustration in FIG. 1A shows a memory chip 6 used as memory; however, any suitable memory may be used, including RAM, ROM, flash drive, or memory card. The embodiment of FIG. 1A illustrates an electronic interface 116 that may be used to transfer stored information between the cartridge 100 and a sampler or a personal computer ("PC").

Another embodiment of a cartridge 200 is shown in FIG. 2A and in cross-section in 2B. Cartridge 200 may include the same or similar features as cartridge 100, and consistent numbering is used wherever possible. For example, cartridge 200 may include an inlet 202 and outlet 204 connected to a sorbent tube 214. The inlet 202 and outlet 204 may automatically seal the cartridge 200 closed when it is not connected to a sampler 300, 400 or an analytical instrument 600. As illustrated in FIG. 2B, cartridge 200 may use spring force for self-sealing. A spring 208 mounted in a cartridge 200 maintains a bearing or valve ball 210 in a normally closed position against valve seat 212. When the cartridge 200 is inserted into a sampler 300, 400, the spring 208 is compressed; thereby opening inlet 202 and/or outlet 204. This embodiment also illustrates an electronic interface 216 that may be used to transfer information between the cartridge 200 and a sampler or a PC. The cartridge 200 may further include a heater 217 and a thermocouple 219 configured to heat and measure the temperature of analytes within the tube 214. Additionally, the cartridge 200 may include a clip 205 configured to secure the cartridge within a sampler, PC, or other desired device.

A sampler may be used in conjunction with the cartridge to obtain a sample for eventual analysis. In one implementation, the sampler is a small, lightweight, battery 46 operated device that can easily be transported to an area of possible contamination. FIGS. 3A-3G illustrate one embodiment of such a sampler 300 having a "pistol" shape. FIGS. 4A-4D illustrate another embodiment of such a sampler 400 having shape similar to a personal digital assistant ("PDA"). FIGS. 5A-5B illustrate yet another embodiment of a sampler 500. Samplers 300, 400, and 500 may include the same or similar features, and consistent numbering is used wherever possible.

Figure 3A:
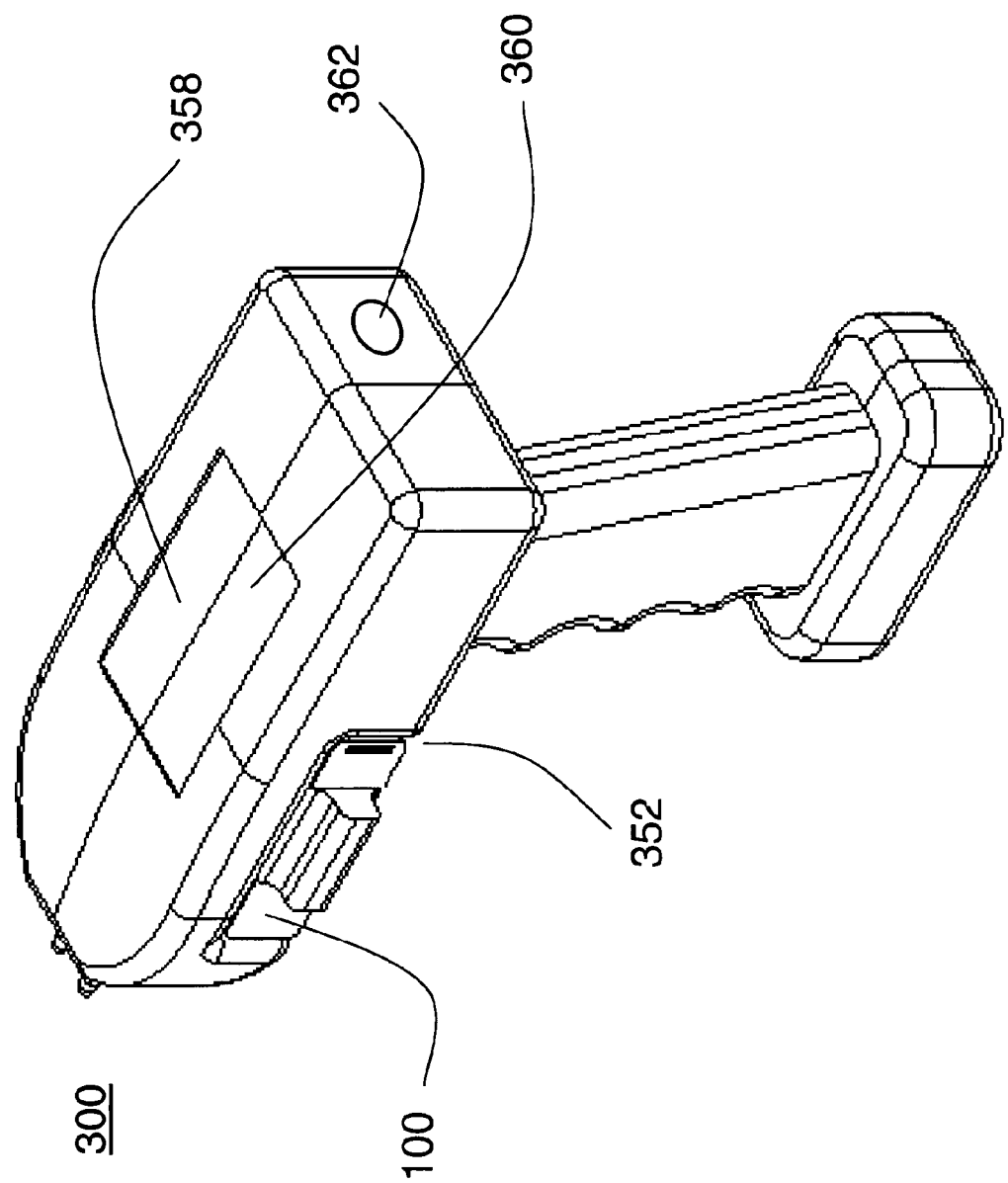
FIG. 3A is a perspective view of a handheld sampler with a cartridge installed in accordance with one embodiment.
Figure 3B:
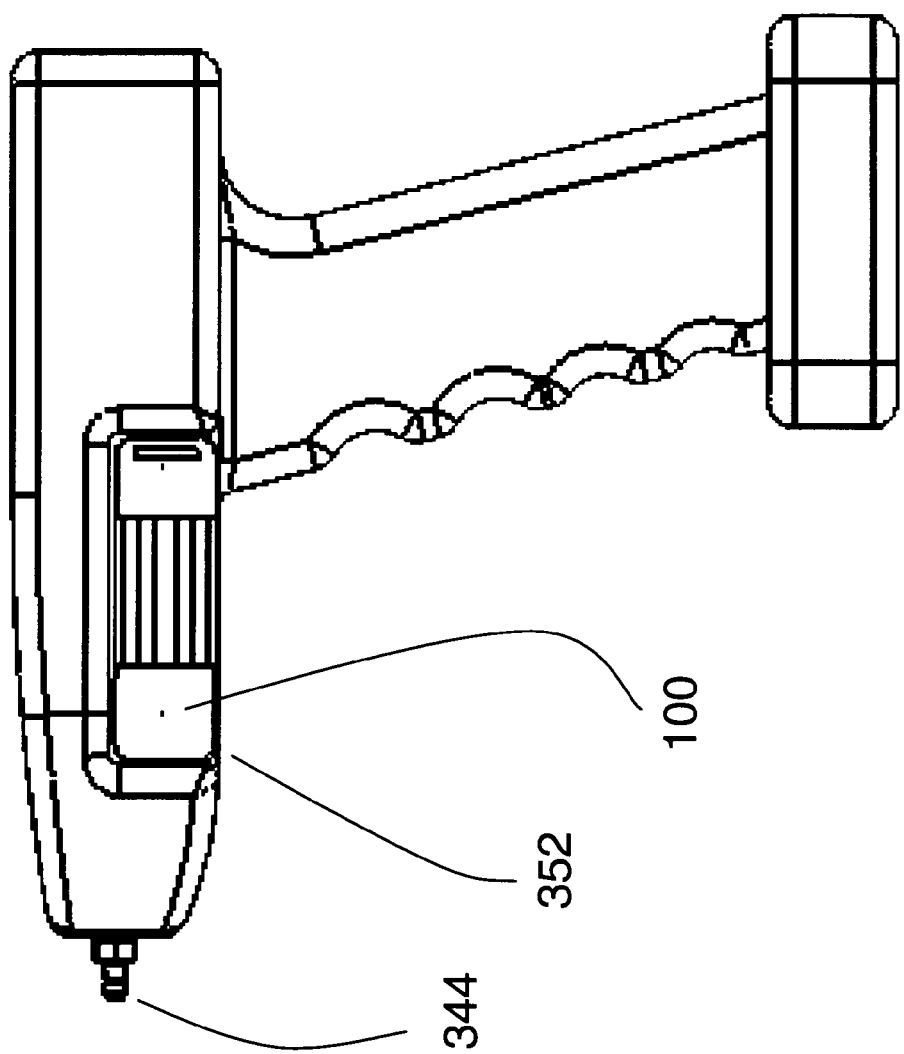
FIG. 3B is a side view of a handheld sampler with a cartridge installed in accordance with one embodiment.
Figure 3C:
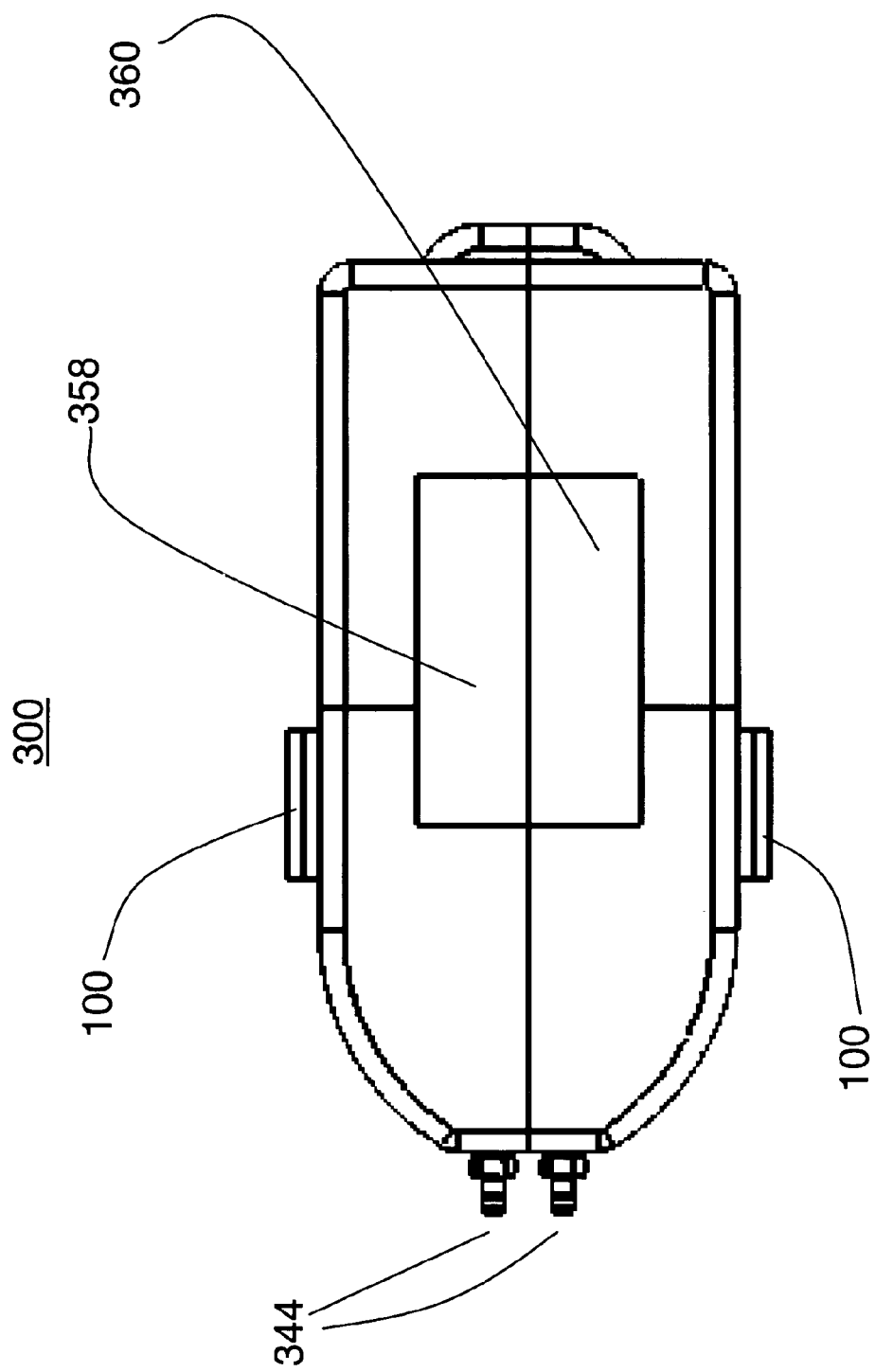
FIG. 3C is a top view of a handheld sampler with a cartridge installed in accordance with one embodiment.
Figure 3D:
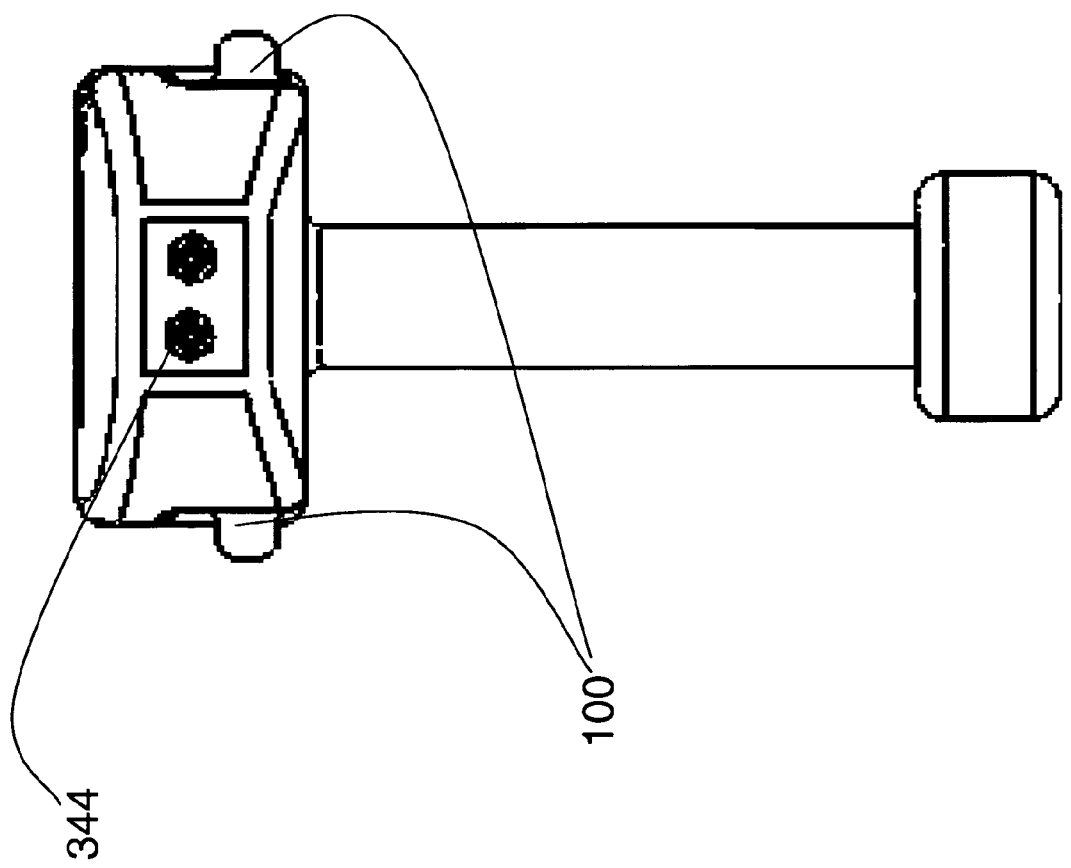
FIG. 3D is a front view of a handheld sampler with a cartridge installed in accordance with one embodiment.
Figure 3E:
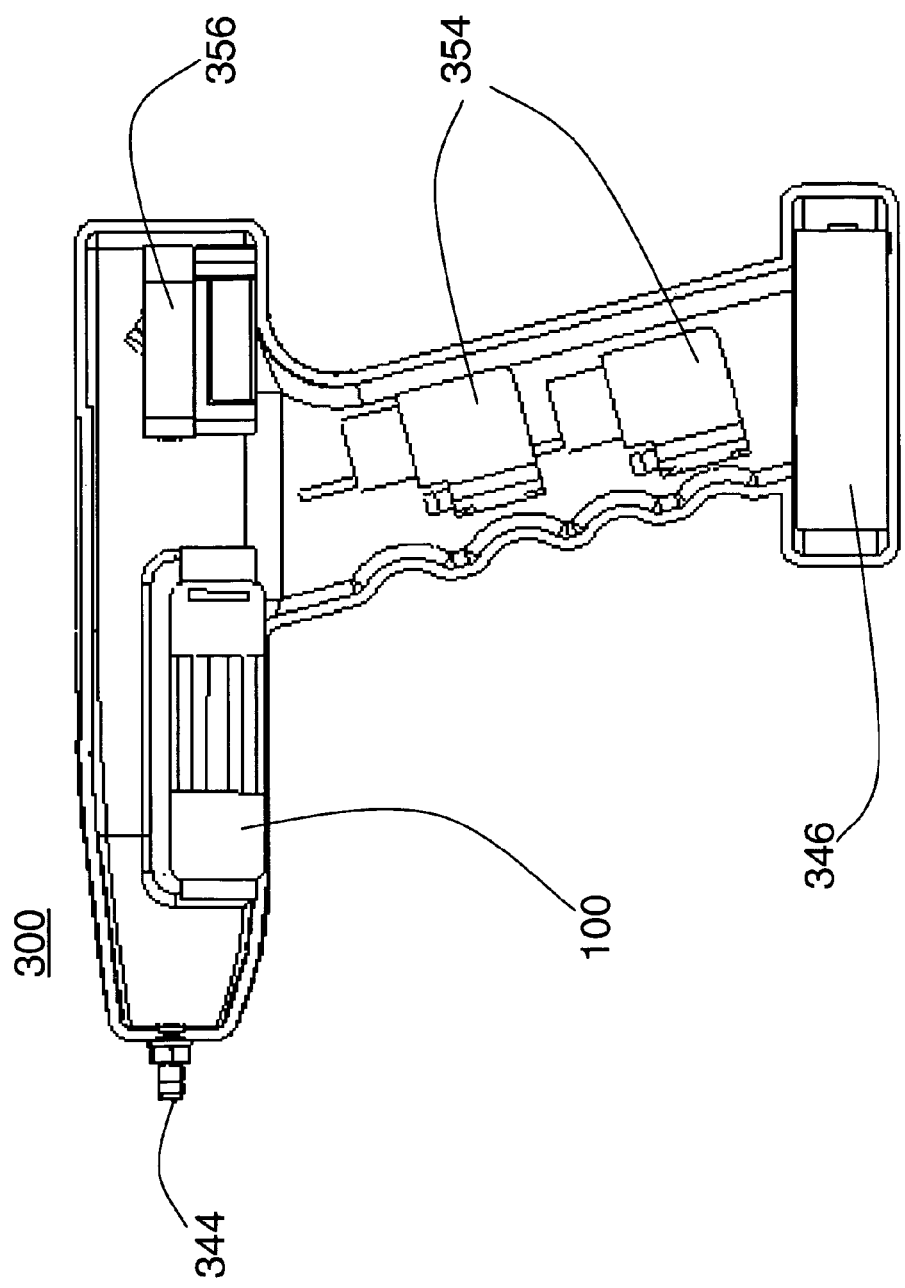
FIG. 3E is an interior side view of a handheld sampler with a cartridge installed in accordance with one embodiment.
Figure 3F:
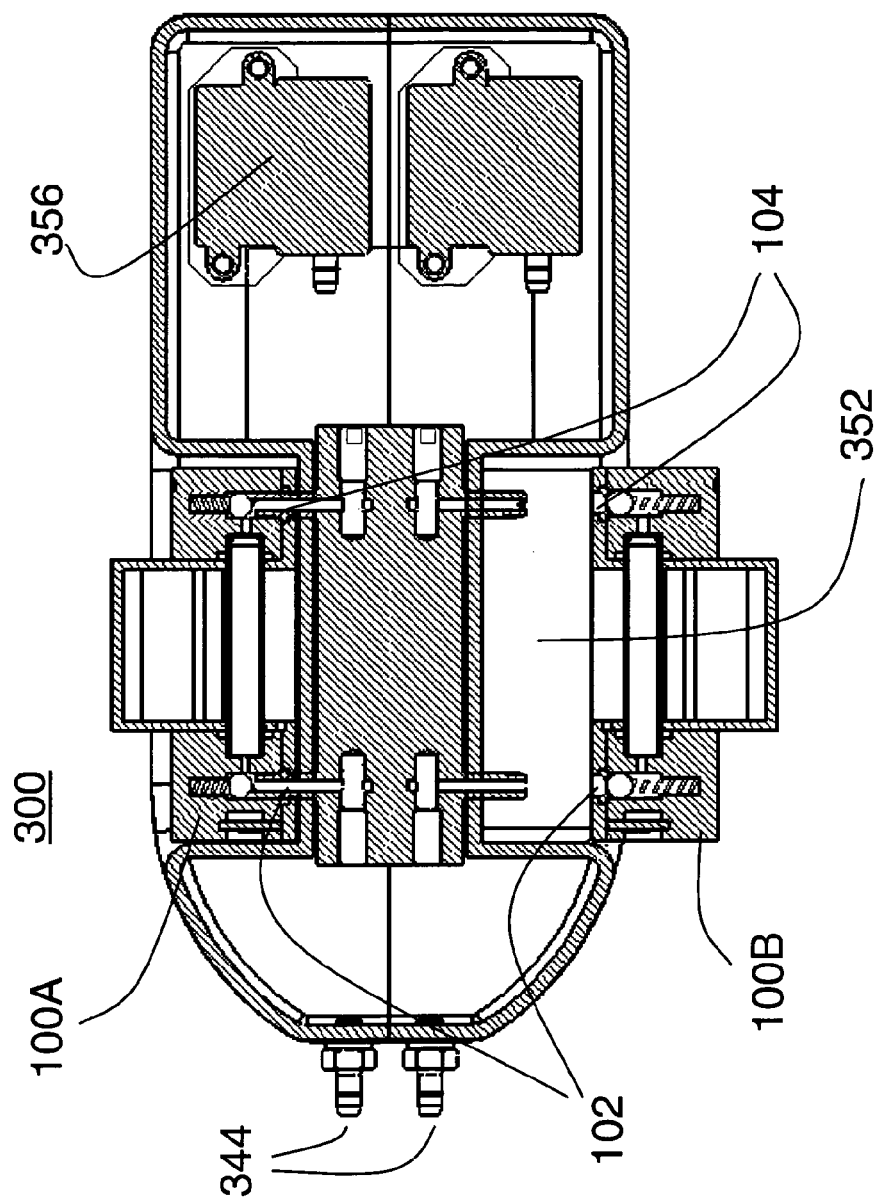
FIG. 3F is a second interior top view of a handheld sampler with a cartridge installed in accordance with one embodiment.
Figure 3G:
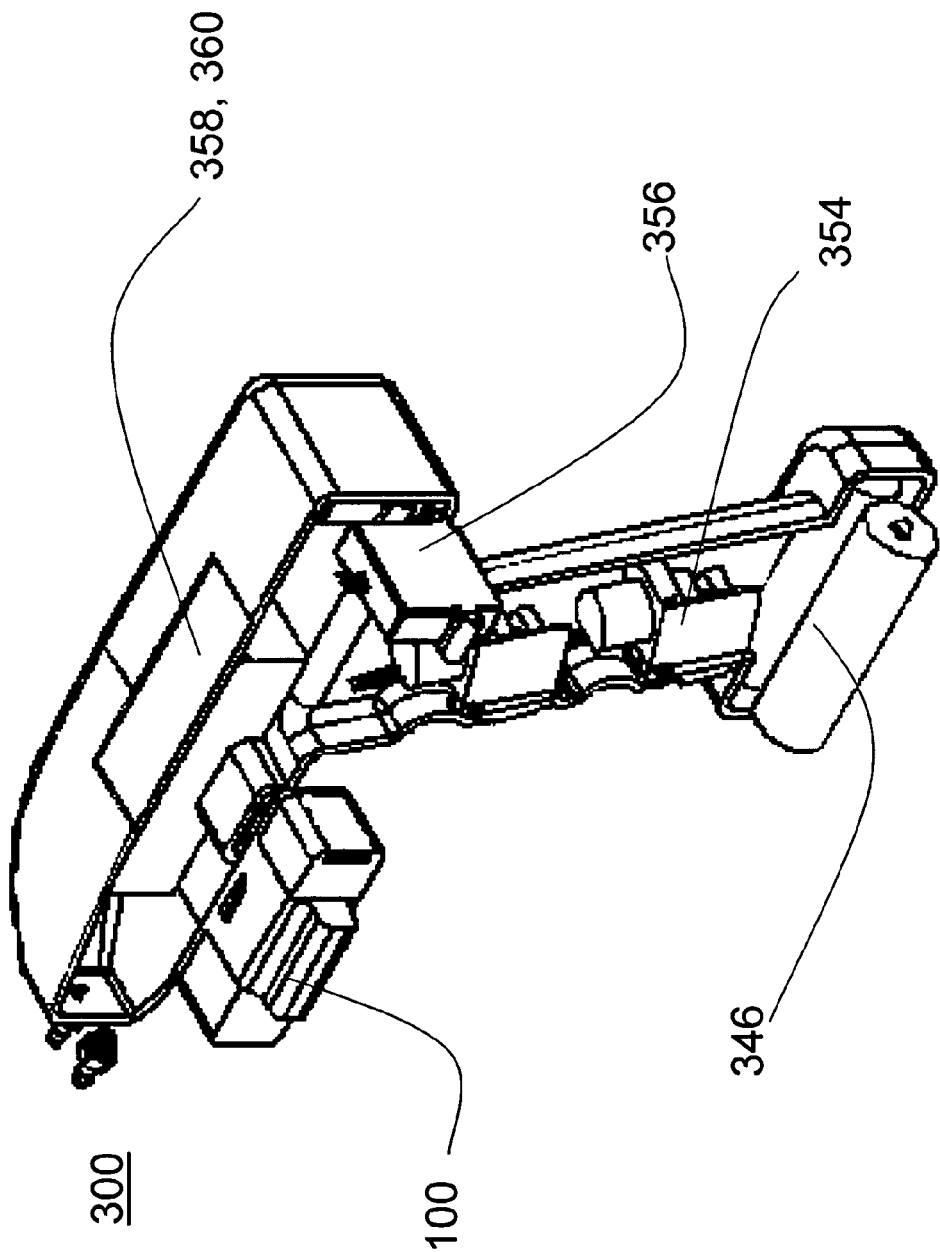
FIG. 3G is a perspective cut-away view of a handheld sampler with a cartridge installed in accordance with one embodiment.

The sampler 300 may include a docking port 352 to accept the sampling cartridge 100, as shown in FIGS. 3A and 3F. In a similar fashion, cartridge 100 may insert into sampler 400 (as shown in FIGS. 4B-4C) and cartridge 200 may insert into sampler 500 (as shown in FIG. 5A). The docking port 352 will open the sealed fluidic ports of the cartridge 100 and will connect with the electronic interface 116 of the sample cartridge. FIG. 2G illustrates two cartridges 100A and 100B in different states of insertion. Cartridge 100A is fully inserted into the sampler 300, thereby opening the inlet 102 and outlet 104 ports of the cartridge 100A. Cartridge 100B is substantially removed from the sampling dock 352, leaving inlet 102 and outlet 104 ports closed.

Figure 7:
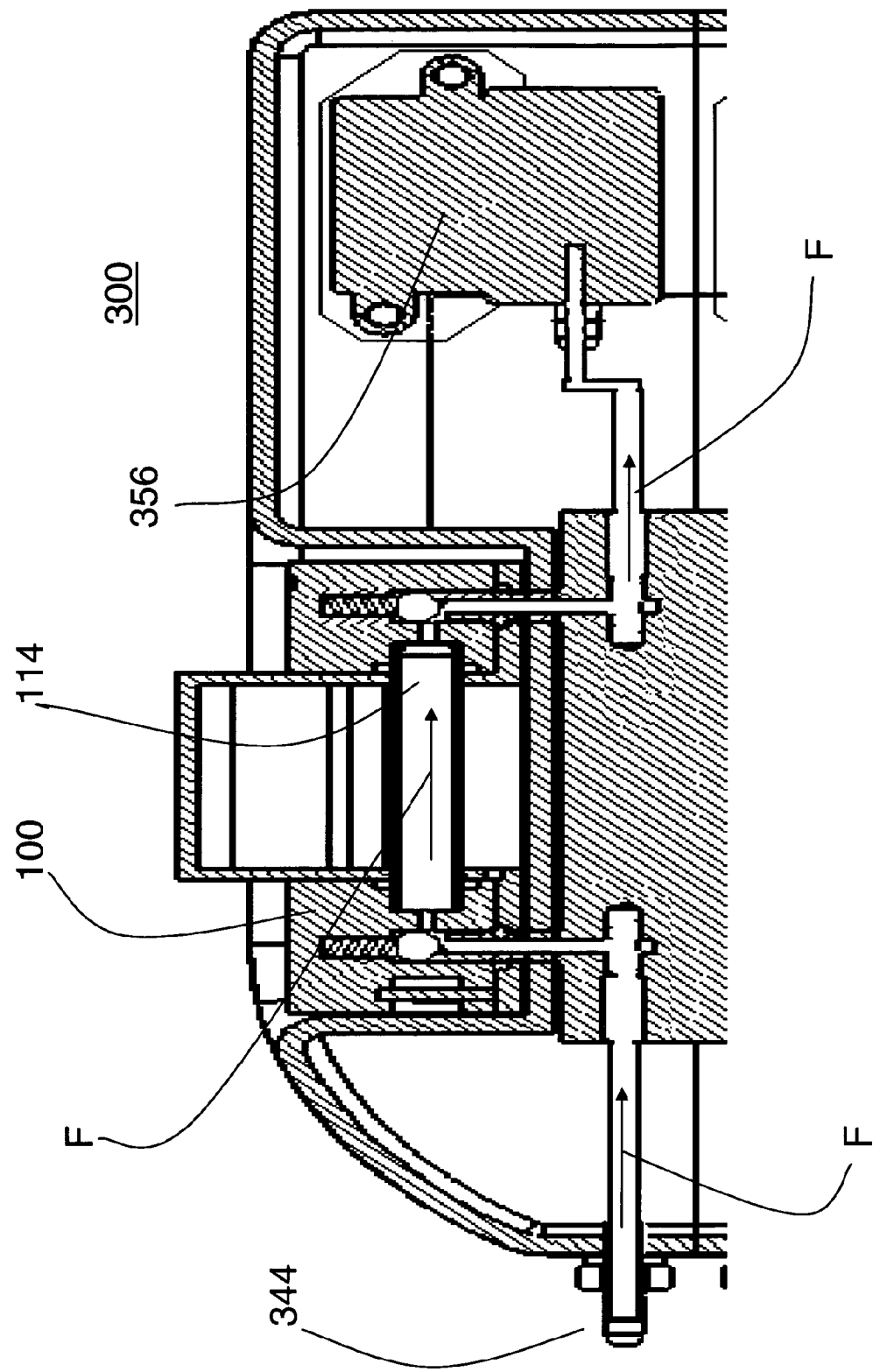
FIG. 7 is partial interior top view of a handheld sampler with a cartridge installed in accordance with one embodiment, illustrating the flow of a sample.
Figure 8:
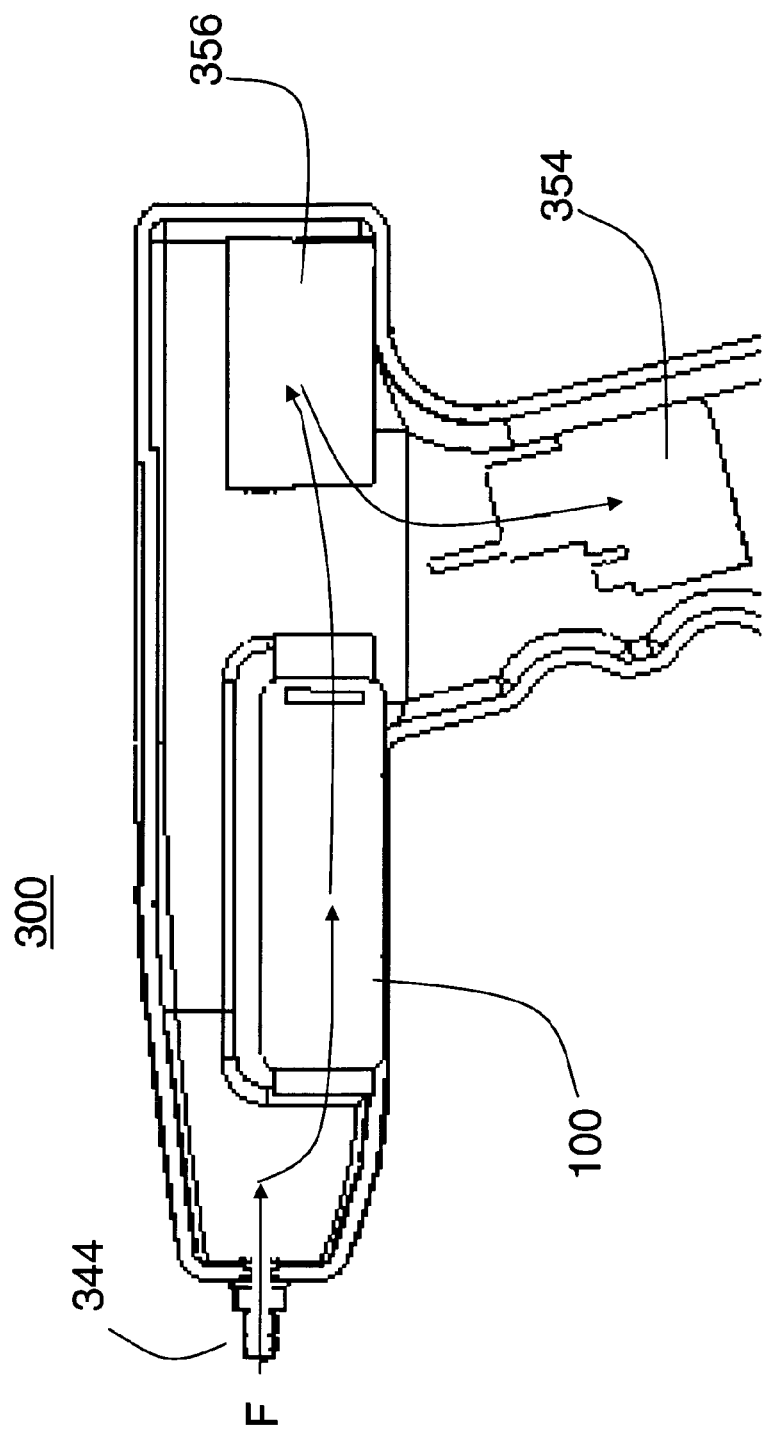
FIG. 8 is a side view of a handheld sampler with a cartridge installed in accordance with one embodiment, illustrating the flow of a sample.

As shown in FIG. 3E, in one implementation, the sampler 300 will include a sample pump 354 to pull air through the cartridge 100 via a sampler inlet 344 and will include a flow/volume sensor 356 to measure the sample volume. The sampler 300 may have one or multiple sample flow paths F to allow for sampling of sequential or simultaneous sampling of multiple cartridges 100, as shown in FIGS. 7 and 8. In one implementation, the sampler may include a filter (not shown) disposed at a point upstream of sample cartridge 100 to filter debris and other solid or liquid particulates as desired. Such filters are also well-known in the art. In one aspect, the sample pump 354 may be adapted to draw in volumes of matter in other than a gaseous state. The intake system may be adapted to draw in, for example, gasses bearing solid or liquid particulates, liquids, or colloidal suspensions.

In one implementation, the sampler 300 may include a CPU, display 358, and/or keypad 360, as shown in FIG. 3A. The keypad 360 may be used to select an operation mode or to enter data about the sample or sample cartridge 100. Once a particular operation mode is selected, the CPU will cause the sampler 300 to run in the selected operation mode. Different operation modes may be selected that operate the apparatus according to varying parameters. For example, an operation mode may be selected that operates the sample pump 354 for a predetermined length of time. Another operation mode may be selected that operates the sample pump 354 until a predetermined volume of gas has passed through the flow meter. Various operation modes may be programmed into the memory by a user, as unique operation modes are developed. Alternatively, the apparatus may be operated manually. The display 358 may be used to display information related to operation of the sampler 300 as well as other information about the sample, sample cartridge 100, or the environment. In one implementation in which the cartridge 100 includes memory 106 for storing data, the sampler 300 will record critical information pertinent to the sample collected including GPS location when sampled, volume of sample collected, date/time stamp, voice data, and image data to the sampling cartridge 100 for use when it is later analyzed.

In one implementation, the sampler 300 will also include an interface 362 (FIG. 3A) to connect the sampler 300 to an analytical instrument 600 or a PC. This connection will allow for programming a smart sampler 300. Multiple programmable options will be available to collect samples based on time, volume, or manual control by an operator.

In yet another implementation, the sampler 300 will be outfitted with a chemical trigger technology to let the user know when it is likely that a chemical of interest exists in the environment and should be sampled. In one implementation, the sampler 300 may include a FAIMS (high-Field Asymmetric waveform Ion Mobility Spectrometry) detector, a Photo Ionization Detector, or a Metal Oxide Detector, to detect the presence of chemicals in the atmosphere in order to alert the user to obtain a sample. These implementations are merely exemplary and other triggers may be used.

Additional sampler embodiments 400, illustrated in FIGS. 4A-4D, may operate similarly to the embodiments illustrated in FIGS. 3A-3G, and may include similar components. For example, sampler 400 may include a pump 454, flow/volume sensor 456, inlet port 444, display 458, and keyboard 460.

Further sampler embodiments 500, illustrated in FIGS. 5A-5B, may also operate similarly to the embodiments illustrated in FIGS. 3A-3G. Sampler 500 may include a display 558, keyboard 560, inlet ports 544, a pump 554, and a flow/volume sensor 556. Sampler 500 may accept cartridge 200 as previously described.

FIG. 6 depicts an analytical instrument 600. The analytical instrument 600 is used to perform a chemical analysis on the analytes in the sample cartridge 100, 200. The analytical instrument 600 may be any instrument for performing chemical analysis such as a mass spectrometer (MS) or a flame ionization detector (FID). Alternatively, the analytical instrument 600 may be a chemical separation device, such as, e.g., a gas-chromatograph (GC). The analytical instrument 600 may also be a combination GC/MS, GC/electron capture detector (ECD), or GC/FID.

In one implementation, the analytical instrument 600 will have a docking port 682 to mate with the sample cartridge 100, 200. This port will open the sealed fluidic ports of the cartridge 100, 200 and will connect with the electronic interface 116, 216 of the sample cartridge 100, 200. In one implementation in which the cartridge 100, 200 includes memory 106, 206 for storing data, when the cartridge 100, 200 is attached to the instrument it will access any data stored on the cartridge's 100, 200 memory chip 106, 206. This data will be downloaded to the instrument when the cartridge 100, 200 is analyzed. This data can be used to complete a quantification analysis and will provide a direct line chain of evidence for important information documented at the point of sample collection. In one implementation, the instrument may also include a cartridge (not shown) that can be used as an external standard to calibrate the sample.

Other embodiments will be apparent to those skilled in the art from consideration of the specification and practice of the disclosure herein. It is intended that the specification and examples be considered as exemplary only, with a true scope and spirit of the disclosure being indicated by the following claims.

What is claimed is:

1. A portable sampler for collecting a sample, the portable sampler comprising:
 a portable housing having an interior portion, wherein the portable housing is configured to removably secure a sample cartridge within the interior portion, the sample cartridge having a self-sealing inlet port and a self-sealing outlet port, the portable housing further configured to open the self-sealing inlet port and the self-sealing outlet port when the sample cartridge is secured therein;
 a sample inlet in communication with an area outside the housing and configured to establish fluid communication with the sample cartridge when the sample cartridge is secured;
 a pump configured to draw a sample into the sample cartridge through the sample inlet when the sample cartridge is secured;
 a processor configured to operate the sampler;
 an input/output interface; and
 a detection trigger configured to detect the presence of at least one predetermined chemical, the processor being further configured to take a sample when the detection trigger detects the presence of the at least one predetermined chemical.

2. The sampler of claim 1, further comprising a sample cartridge, the sample cartridge further comprising:
 an inlet port in fluid communication with the sample inlet and configured to self-close when the inlet port is not in use;
 an outlet port configured to self-close when the outlet port is not in use; and
 a sample retention portion in fluid communication with and disposed between the inlet port and outlet port and adapted to trap an atmospheric sample.

3. The sampler of claim 2, further comprising a filter configured to filter the sample before the sample is drawn into the sample cartridge.

4. The sampler of claim 1, wherein the input/output interface further comprises a keypad.

5. The sampler of claim 1, wherein the input/output interface further comprises a display.

6. The sampler of claim 1, further comprising a flow sensor.

7. The sampler of claim 1, further comprising a connector for communicating information with a computer.

8. The sampler of claim 1, wherein the portable housing is further configured to removably secure a plurality of sample cartridges within the interior portion.

9. The sampler of claim 8, wherein the sampler defines a plurality of separate and independent flowpaths between the sample inlet and each of the plurality of sample cartridges when the plurality of sample cartridges is inserted.

10. The sampler of claim 1, wherein the detection trigger is a chemical detection trigger.

11. The sampler of claim 1, further comprising an electronic interface configured to couple with an interface of the sample cartridge.

12. The sampler of claim 11, wherein the interface is coupled to the processor and is configured to provide electronic data to the sample cartridge.

* * * * *